(12) United States Patent
Kim et al.

(10) Patent No.: US 8,945,149 B2
(45) Date of Patent: Feb. 3, 2015

(54) AUTOMATED SURGICAL ILLUMINATION SYSTEM

(76) Inventors: Gabriel Min Kim, West Friendship, MD (US); Tiffany Litien Chen, Atlanta, GA (US)

( * ) Notice: Subject to any disclaimer, the term of this patent is extended or adjusted under 35 U.S.C. 154(b) by 478 days.

(21) Appl. No.: 13/440,983

(22) Filed: Apr. 5, 2012

(65) Prior Publication Data

US 2012/0259178 A1     Oct. 11, 2012

Related U.S. Application Data

(60) Provisional application No. 61/471,714, filed on Apr. 5, 2011.

(51) Int. Cl.
*A61B 19/00* (2006.01)
*A61B 19/04* (2006.01)

(52) U.S. Cl.
CPC ............. *A61B 19/04* (2013.01); *A61B 19/5202* (2013.01); *A61B 2019/5255* (2013.01); *A61B 2019/5437* (2013.01); *A61B 2019/5479* (2013.01)

USPC ........... 606/130; 362/572; 600/249; 600/472; 606/2; 606/102

(58) Field of Classification Search
CPC ............. A61G 15/00; A61G 7/00; A61B 1/06
USPC ............... 362/572; 606/2, 102, 130; 600/249, 600/472–480; 356/614
See application file for complete search history.

(56) References Cited

U.S. PATENT DOCUMENTS

2006/0044800 A1*  3/2006  Reime ........................... 362/276
2011/0118782 A1*  5/2011  Kashey ......................... 606/235

OTHER PUBLICATIONS

I. Golovinova, Written Opinion of the International Searching Authority, PCT/ISA/237, Jun. 13, 2012, 1-4.
I. Golovinova, International Search Report, PCT/ISA/210, Jun. 13, 2012, 1-3.

* cited by examiner

*Primary Examiner* — Anabel Ton

(57) ABSTRACT

The present invention provides illumination for a surgical procedure. Using an optical tracking system, the illumination is made to automatically track an optical marker on a surgical glove worn by a clinician to provide more consistent illumination for a surgical procedure.

20 Claims, 7 Drawing Sheets

AUTOMATED SURGICAL ILLUMINATION SYSTEM

CROSS-REFERENCES

The present application claims the benefit of priority to U.S. Provisional Application No. 61/471,714 (filed 5 Apr. 2011), which is incorporated by reference herein.

TECHNICAL FIELD

The present invention relates to surgical lighting systems.

BACKGROUND OF THE INVENTION

It is generally believed that it would be desirable to produce a surgical lighting system that can eliminate the need for a surgeon or scrub nurse to manually move a surgical light with their hands to provide focused lighting at the surgical site. Such a system would prevent undue contamination of instruments as a result of transfer of bacterium from lamp handles, allow surgical personnel to focus their attention to more important tasks such as instrument passing, and alleviate the need for low-hanging, reachable lamp handles which may obstruct the surgical flow.

There exist several different approaches to alleviate this problem. U.S. Pat. No. 5,093,769 by Luntsford discloses a surgical lighting system which is remotely controlled by surgical personnel. This system is also capable of "recording" a sequence of lamp configurations which can be "played back" during time of surgery. Another solution as disclosed in U.S. Pat. No. 6,560,492 by Borders describes a system which can control several aspects of operating room function such as: patient table movement, temperature control, and lighting intensity. The solution by Luntsford eliminates the need for surgical personnel to manually move surgical lamps by allowing them to remotely control the lamps, but does not totally eliminate the need to have surgical personnel to initiate such movements, and is therefore only semi-automatic. The solution by Borders suffers from a similar downside, as a user is required to control the disclosed system. Border's solution offers to modulate the intensity of the surgical lights, but does not allow for movement of said lights.

The system disclosed in U.S. Pat. No. 6,642,836 by Wang et al discusses a device which utilizes voice recognition to control various machines in the operating room including lights. However this system still requires a surgeon or assistant to initiate the lamp movement using their voice, and is thus only semi-automatic. Also, the voice recognition system introduces the complication of voice-recognition which may not always be accurate.

SUMMARY

The present invention provides illumination for a surgical procedure. Using an optical tracking system, the illumination is made to automatically track an optical marker on a surgical glove worn by a clinician to provide more consistent illumination for a surgical procedure.

The present invention uses a surgical glove that comprises an optical marker that can be detected by an optical sensor. The optical marker may be an active optical marker that emits light in any suitable wavelength range, including infrared. Any suitable light-emitting source may be used. For example, the optical marker may be a light-emitting diode (LED). This active optical marker can be switched on or off when desired by the user (such as a surgeon). Alternatively, the optical marker may be a passive marker that reflects light received from an external source. In some cases, the passive marker may be an infrared reflector.

In one embodiment, the present invention provides a surgical lighting system that comprises a lighting apparatus. The lighting apparatus comprises a movable platform and an illumination source on the movable platform. The illumination source provides visible light for performing surgical procedures. The movable platform can be moved to change the direction of the illumination. The lighting apparatus further comprises a motor for moving the movable platform to change the direction of the illumination source. There is a controller operably coupled to the motor and an optical sensor operably coupled to the controller. The automatic operation of the surgical lighting system can be switched on or off by two methods: (a) Switching on or off the controller of the lighting apparatus; or (b) Switching on or off the active optical marker.

The optical sensor detects the light emitted or reflected by an optical marker on a surgical glove. The controller operates the motor based on information received from the optical sensor to direct the illumination source towards the glove.

The controller may use any suitable tracking, searching, or positioning algorithm. For example, the lighting apparatus may comprise an array of sensors (e g infrared sensors) surrounding the illumination source and arranged in a radial and equidistant pattern from a fixed point. The general direction of movement or placement of the optical marker on the gloved hand can be determined by reading the intensity values and determining the largest intensity value from the array of sensors. In response to the sensor readings, motors on the lighting system move the platform so that the illumination source points in the direction corresponding to the sensor giving the highest intensity reading.

In embodiments where the optical marker on the glove is an infrared reflector, the system may rely on an infrared source on the lighting apparatus for providing the infrared emissions. The infrared source may be the same as the illumination source (e.g. the illumination source includes infrared emissions) or a separate component of the lighting apparatus.

In another embodiment, the present invention provides a method of providing illumination for a surgical procedure. The method comprises providing a lighting apparatus of the present invention. The method further comprises providing either (a) a surgical glove and an optical marker for attaching to the glove, or (b) a surgical glove comprising an optical marker. The optical sensor detects the light emitted or reflected by the optical marker on the surgical glove. The controller operates the motor based on information received from the optical sensor to direct the illumination source towards the glove.

In another embodiment, the present invention provides a method of performing a surgical procedure. In this method, the clinician places a surgical glove that comprises an optical marker on a hand. The clinician moves the gloved hand while performing the surgical procedure. The method further comprises using a lighting apparatus of the present invention. The optical sensor detects the light emitted or reflected by the optical marker on the surgical glove. The controller operates the motor based on information received from the optical sensor to direct the illumination source towards the glove.

In another embodiment, the present invention provides a room for performing a surgical procedure. The room comprises a surgical bed or chair; a surgical glove comprising an optical marker, or a surgical glove and separately, an optical marker for attaching to the glove. The room further comprises a lighting apparatus of the present invention. The optical sensor detects the light emitted or reflected by an optical marker on a surgical glove. The controller operates the motor based on information received from the optical sensor to direct the illumination source towards the glove.

The lighting apparatus is positioned so that it can be directed towards the surgical bed or chair. For example, the lighting apparatus may be fixed to the ceiling, wall, or floor of the room so that it can be directed towards surgical bed or chair.

In another embodiment, the present invention provides a surgical glove comprising an optical marker. Being a surgical glove, the glove may have one or more of the following characteristics: sterile, elastic, conforms tightly to a person's hand, made of latex or other elastic material, and/or impermeable to body fluids (such as blood, saliva, urine, wound exudate, mucous, etc.). The surgical glove may be used for any suitable medical procedure, including surgical, dental, obstetric, gynecological, and/or dermatological applications. As used herein, surgical procedures include surgical, dental, obstetric, gynecological, veterinary, and/or dermatological procedures.

In another embodiment, the optical marker can be placed on bare hands for other uses. In another embodiment, the glove is not necessarily a surgical glove. For example, the glove could be for semiconductor or industrial uses.

The optical marker may be part of the glove in any suitable way, such as being embedded in the glove, attached to the glove, or part of the glove as a single unitary article. Alternatively, the optical marker may be provided separately for the user to attach to the glove. For example, the optical marker may be an adhesive patch that can be attached to the glove. In one particular example, the optical marker may be an infrared-reflective adhesive patch that can be attached to the outer surface of the glove (e.g. surface for the back of the hand). In another example, an active optical marker could have an adhesive surface for attachment to any surface including the surgical glove.

DETAILED DESCRIPTION

Figure 1:
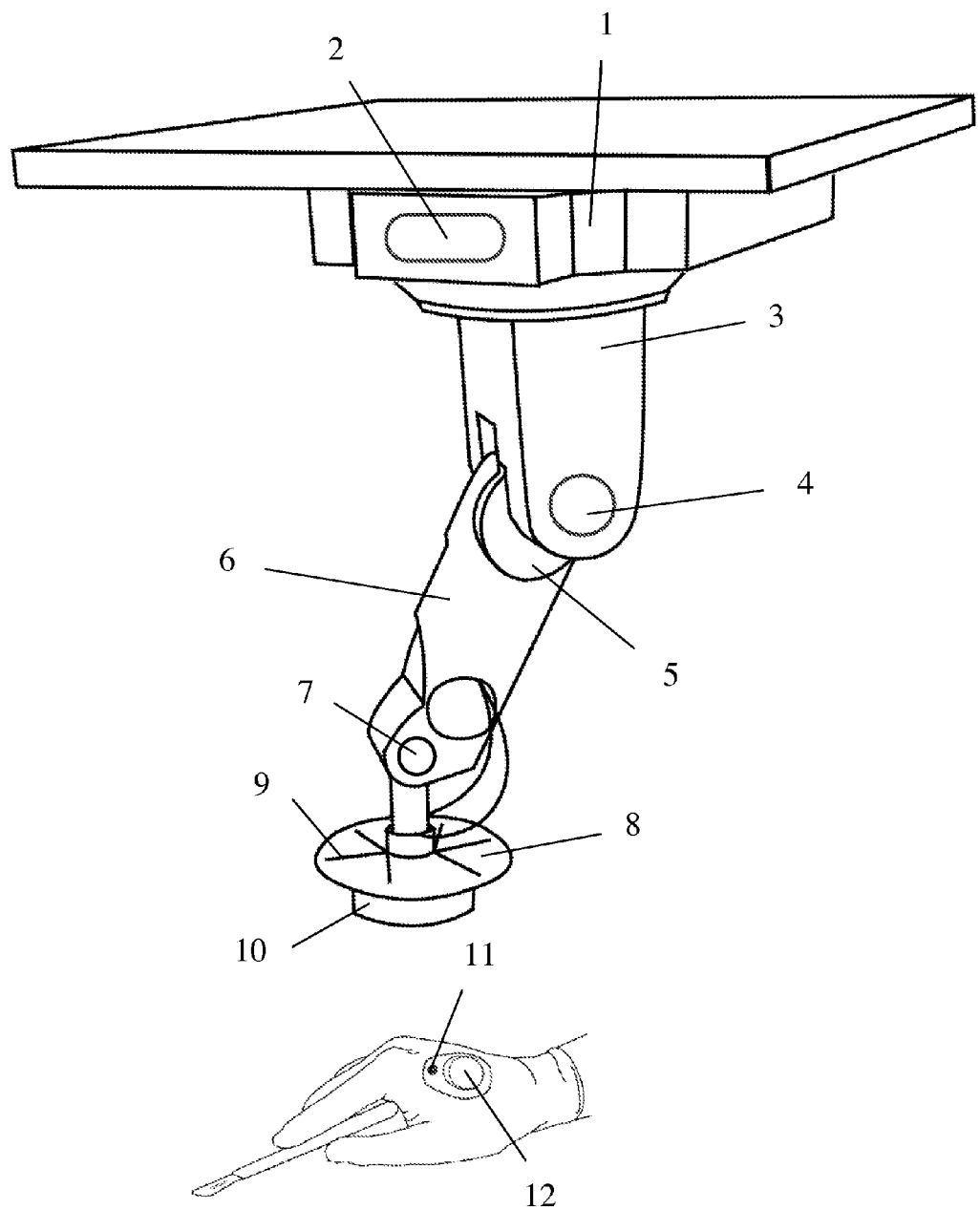
FIG. 1 illustrates the automated surgical illumination system according to the present invention.
Figure 2:
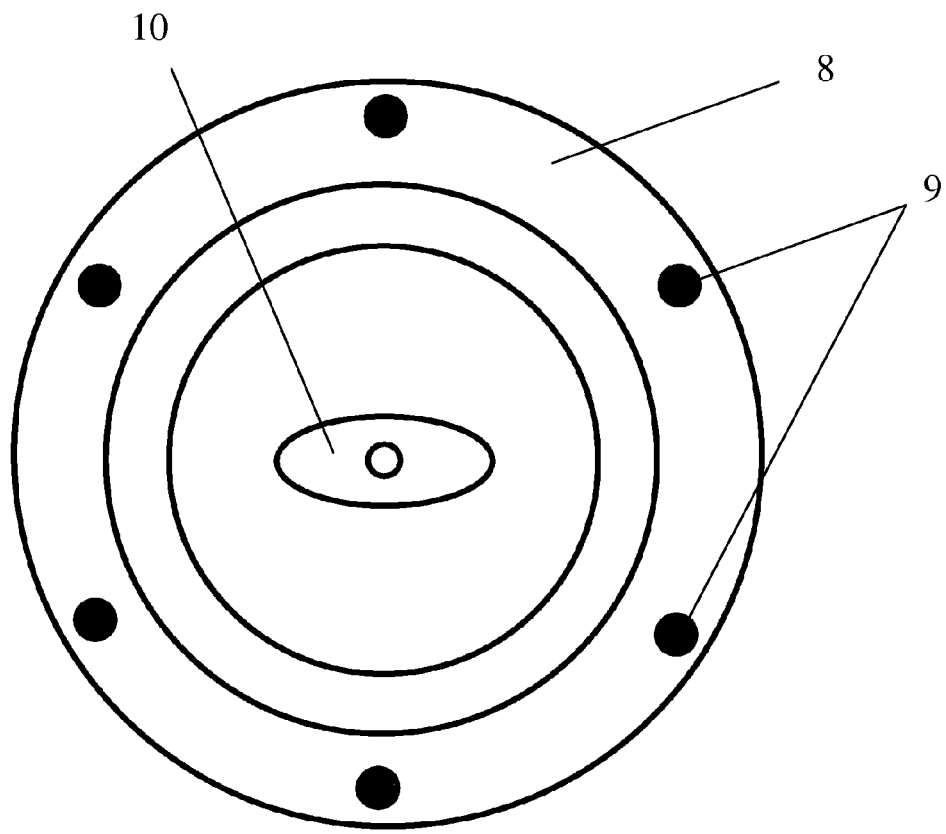
FIG. 2 illustrates to the cone attached to the lower arm of the surgical illumination system as an example of the invention.

FIG. 1 and FIG. 2 illustrate an automated surgical illumination system according to one embodiment of the present invention. The base 1 of the device is to be mounted to the ceiling. Attached to the base 1 is the upper arm segment 3. The upper arm segment 3 rotates 360 degrees both clockwise and counterclockwise on its axis within base 1. Upper arm segment 3 is able to rotate in said manner when motor 2 is turned on in either direction. Attached to the upper arm segment 3 at hinge 5 is lower arm segment 6. Lower arm segment 6 rotates 180 degrees both clockwise and counterclockwise at hinge 5. Lower arm segment 6 is able to rotate in said manner when motor 4 is turned on in either direction. At the end of lower arm attaches a third motor 7 that gives the cone the third range of motion. The lamp reflective cone 8 also functions as a stage for several sensors 9 mounted to the cone 8 to form a sensor array. The light source 10 is affixed and centered inside the reflective cone 8.

An LED emitter (active optical marker) 11 is embedded in a surgical glove worn over the hand. A switch 12 connects and disconnects power to the LED emitter and is worn at a location on the surgeon's hand or body. The said gloved hand is placed underneath the reflective cone 8, which also functions as the sensor array stage.

Figure 3:
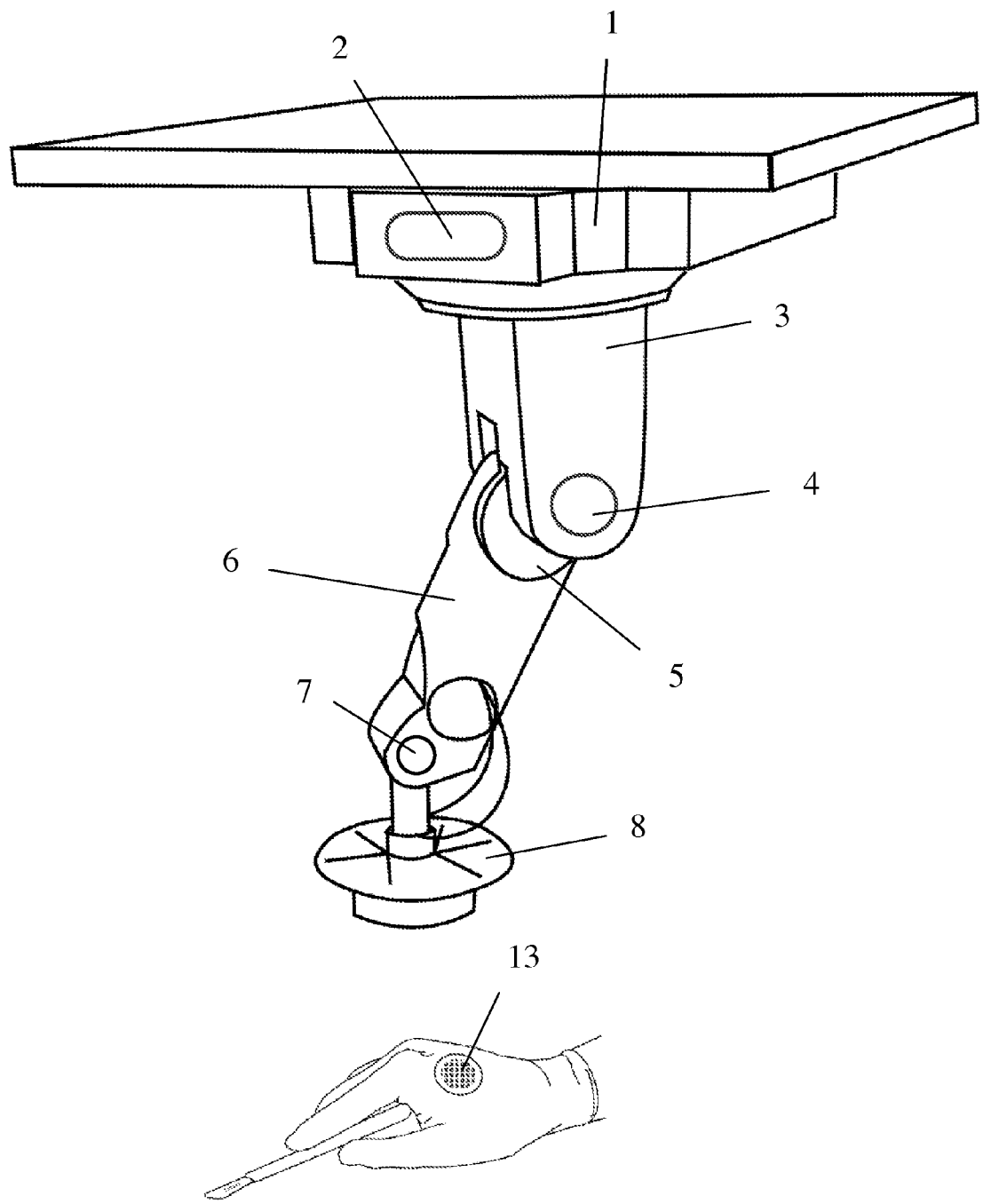
FIG. 3 shows an example lighting apparatus of the present invention.
Figure 4:
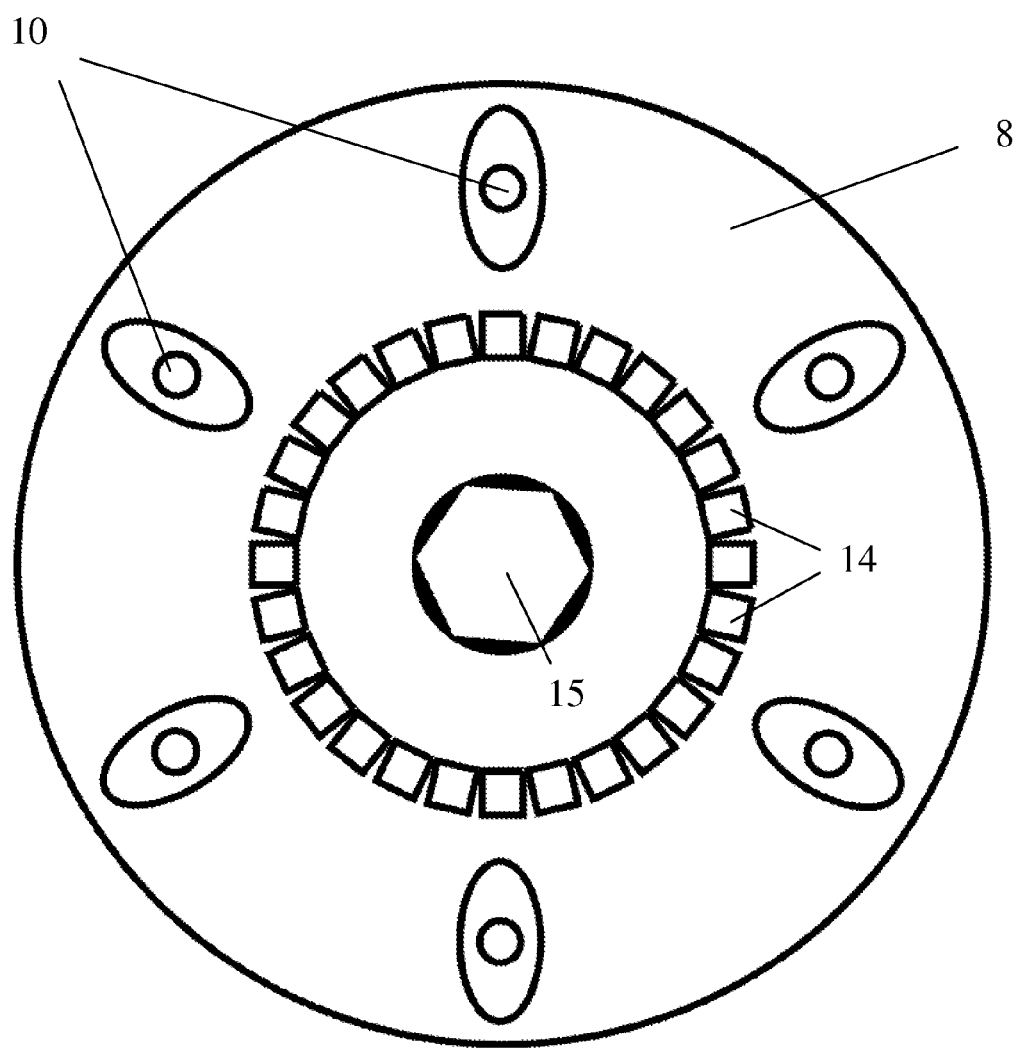
FIG. 4 shows an example illumination source and camera of the present invention.

FIG. 3 and FIG. 4 illustrate another embodiment of the present invention using a passive optical marker. The lamp reflective cone 8 houses several infrared (IR) LEDs 14 and a camera with IR pass filter 15. The light source 10 is affixed outside the IR LEDs 14 and a camera with IR pass filter 15.

An IR-reflective patch 13 is embedded in a surgical glove worn over the hand. The IR-reflective patch 13 reflects the light in the IR wavelength emitted by IR LEDs 14. The camera with IR pass filter 15 then senses the position of the IR-reflective patch.

Figure 5:
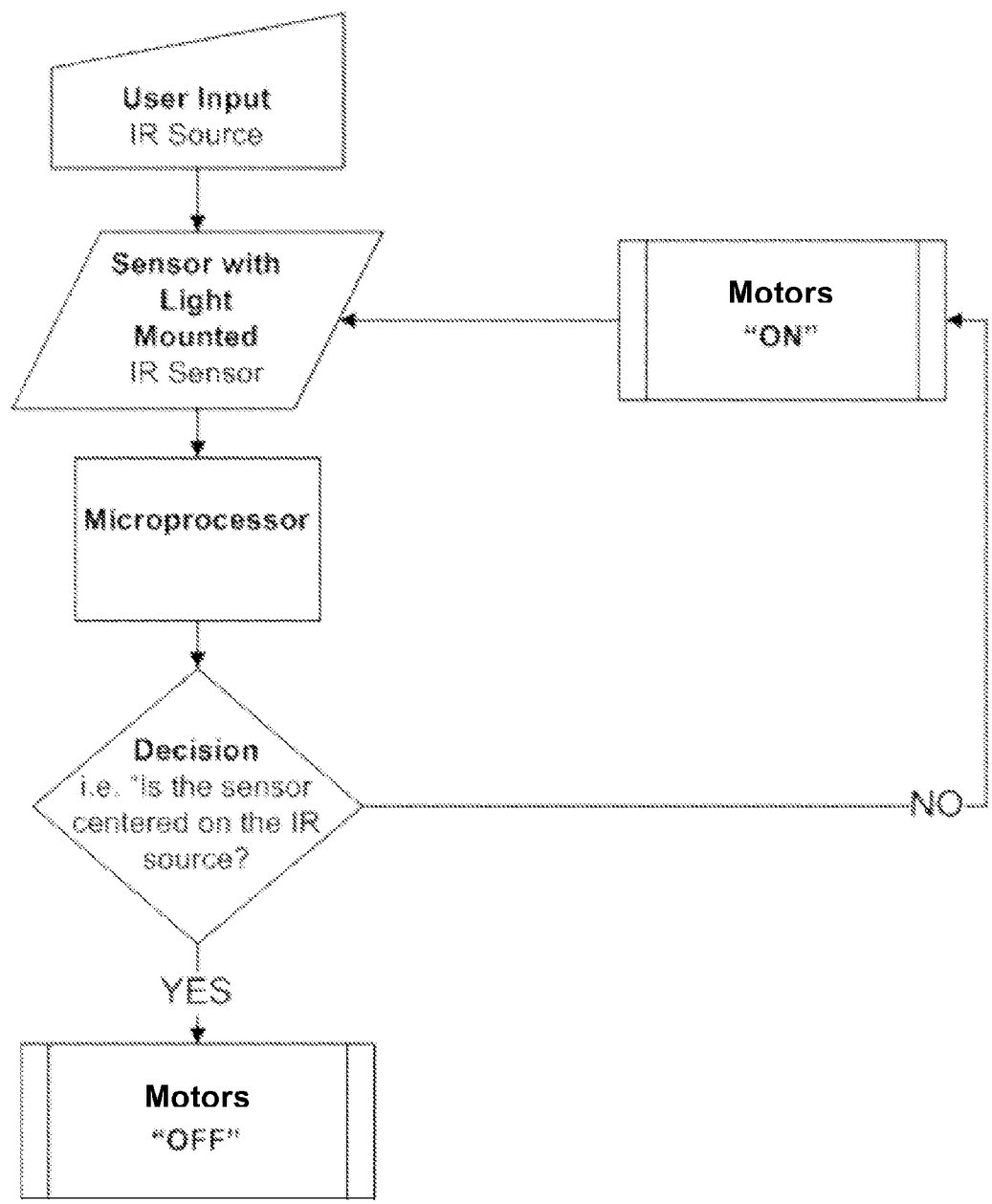
FIG. 5 illustrates a functional schematic diagram of the surgical illumination system in which the invention may usefully practice.

FIG. 5 is a functional schematic diagram of the automated surgical illumination system according to the present invention. This diagram should be taken exemplary of the type of device in which the invention may be embodied, and not as limiting, as it is believed that the invention may usefully be practiced in variety of device implementations including instances where the surgical light is desired to be fixated on a point, thus only tracking when the surgeon initiates tracking. User input comprising of an optical marker (e.g. IR source or IR LED) is detected by the sensor (e.g. IR sensor), which is mounted with the light. The detection in terms of voltage is connected to the input of the microprocessor. Microprocessor makes a calculation and makes a decision whether or not the sensor is centered on the IR source. If the microprocessor makes a decision that the IR sensor is centered on the optical marker, then, the activation of motor stops. However, if the microprocessor decides that the IR sensor is not centered on the optical marker, the motors are activated to center the sensor on the optical marker.

Figure 6:
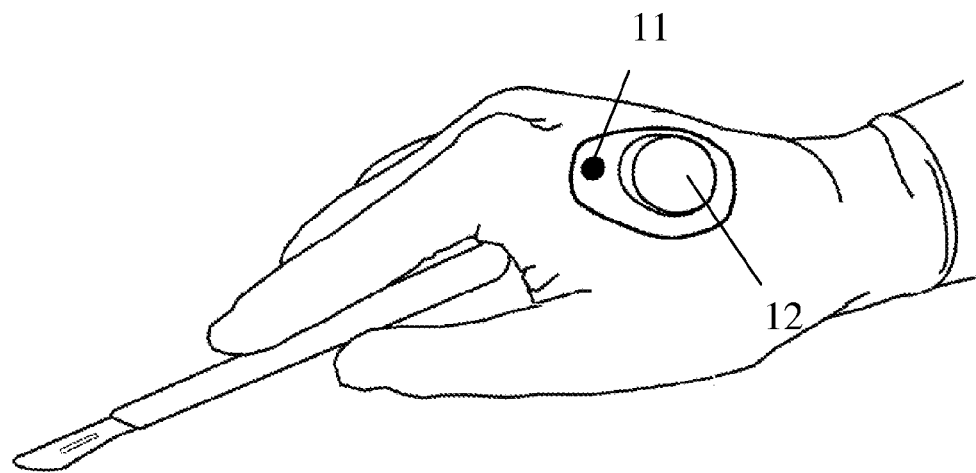
FIG. 6 illustrates two examples of an optical marker used in the present invention.
Figure 6:
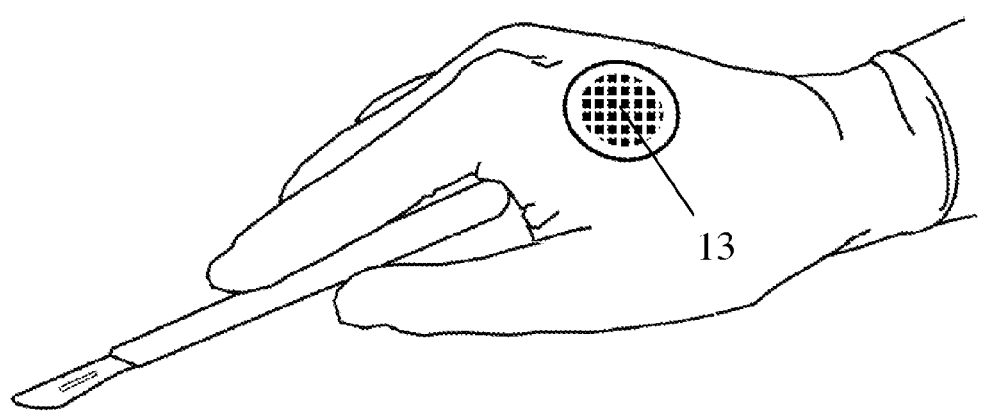

FIG. 6 shows two examples of an optical marker used in the present invention. In one example, an LED emitter (active optical marker) 11 is embedded in a surgical glove worn over the hand in which a switch 12 activates and deactivates the active optical marker 11. In another example, an IR-reflective patch 13 (passive optical marker) attaches to the surgical glove worn over the hand and does not have a switch.

Figure 7:
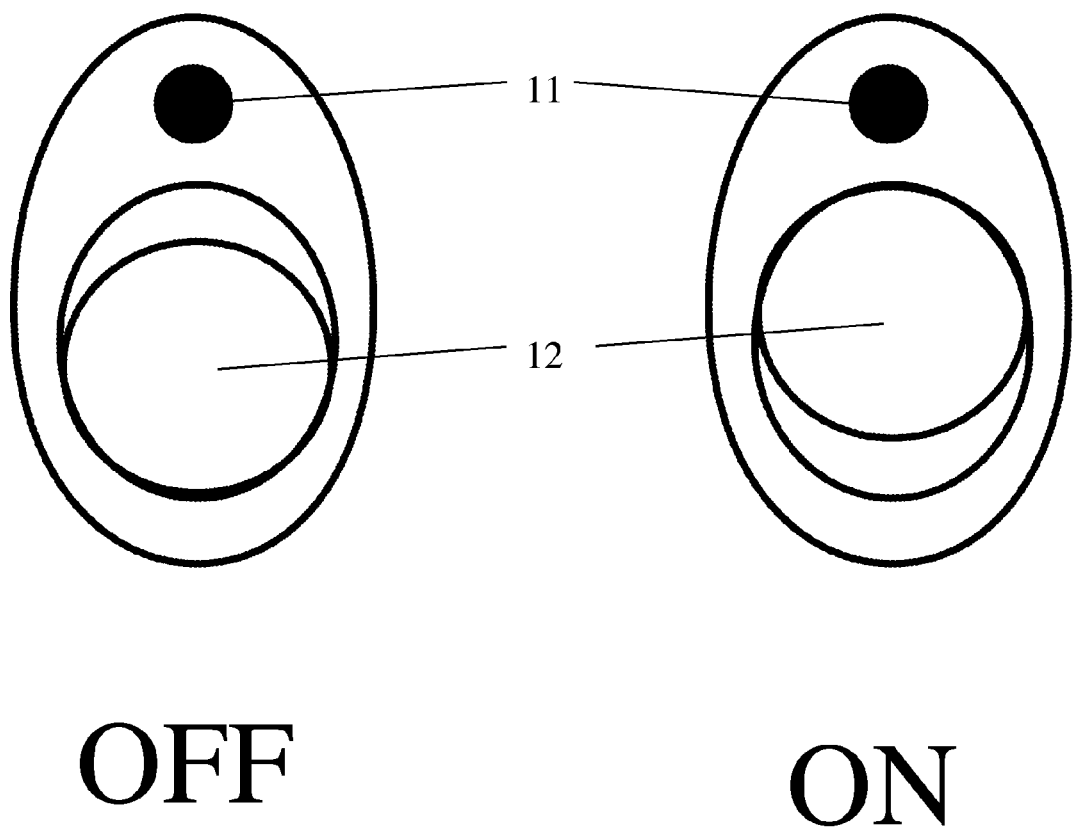
FIG. 7 illustrates an example of a switch that can activate and deactivate an active optical marker.

FIG. 7 illustrates an example of a switch 12 in its on and off position. This switch controls whether the active optical marker is activated or deactivated.

We claim:
1. A surgical lighting system comprising a lighting apparatus, the lighting apparatus comprising:
 a movable platform;
 an illumination source on the movable platform;
 a motor for moving the movable platform to change the direction of the illumination source;
 a controller operably coupled to the motor; and
 an optical sensor operably coupled to the controller;
 wherein the optical sensor detects the light emitted or reflected by an optical marker on a surgical glove; and wherein the controller operates the motor based on information received from the optical sensor to direct the illumination source towards the glove.

2. The lighting system of claim 1, wherein the optical sensor is an infrared sensor.

3. The lighting system of claim 1, further comprising a surgical glove that comprises an optical marker.

4. The lighting system of claim 3, wherein the lighting apparatus further includes an infrared emitting source or the illumination source includes infrared emissions, wherein the optical marker is an infrared reflector, wherein the optical sensor is an infrared sensor that senses the infrared reflections from the infrared reflector of the glove.

5. The lighting system of claim 1, further comprising a surgical glove and separately, an optical marker for attaching onto the glove.

6. The lighting system of claim 5, wherein the lighting apparatus further includes an infrared emitting source or the illumination source includes infrared emissions, wherein the optical marker is an infrared reflector, wherein the optical sensor is an infrared sensor that senses the infrared reflections from the infrared reflector of the glove.

7. A method of providing illumination for a surgical procedure, comprising:
providing a lighting apparatus that comprises:
a movable platform;
an illumination source on the movable platform;
a motor for moving the movable platform to change the direction of the illumination source;
a controller operably coupled to the motor; and
an optical sensor operably coupled to the controller;
providing either (a) a surgical glove and an optical marker for attaching to the glove, or (b) a surgical glove comprising an optical marker;
wherein the optical sensor detects the light emitted or reflected by the optical marker on the surgical glove; and
wherein the controller operates the motor based on information received from the optical sensor to direct the illumination source towards the glove.

8. The method of claim 7, wherein the step of providing the lighting apparatus comprises mounting the lighting apparatus to the ceiling of a room.

9. The method of claim 7, wherein the step of providing the lighting apparatus comprises mounting the lighting apparatus to the wall of a room.

10. The method of claim 7, wherein the step of providing the lighting apparatus comprises mounting the lighting apparatus to the floor of a room.

11. A method of performing a surgical procedure, comprising:
placing a surgical glove on a hand, wherein the surgical glove comprises an optical marker;
moving the gloved hand while performing the surgical procedure;
using a lighting apparatus that comprises:
a movable platform;
an illumination source on the movable platform;
a motor for moving the movable platform to change the direction of the illumination source;
a controller operably coupled to the motor; and
an optical sensor operably coupled to the controller;
wherein the optical sensor detects the light emitted or reflected by the optical marker on the surgical glove; and
wherein the controller operates the motor based on information received from the optical sensor to direct the illumination source towards the glove.

12. The method of claim 11, wherein the step of placing the surgical glove comprises wearing the surgical glove and separately, attaching the optical marker to the surgical glove.

13. A room for performing a surgical procedure, comprising:
a surgical bed or chair;
a surgical glove comprising an optical marker, or a surgical glove and separately, an optical marker for attaching to the glove;
a lighting apparatus comprising:
a movable platform;
an illumination source on the movable platform;
a motor for moving the movable platform to change the direction of the illumination source;
a controller operably coupled to the motor; and
an optical sensor operably coupled to the controller;
wherein the optical sensor detects the light emitted or reflected by an optical marker on a surgical glove; and
wherein the controller operates the motor based on information received from the optical sensor to direct the illumination source towards the glove.

14. A surgical glove comprising an optical marker.

15. The surgical glove of claim 14, wherein the optical marker is a light reflector.

16. The surgical glove of claim 15, wherein the light reflector is an infrared reflector.

17. The surgical glove of claim 16, wherein the infrared reflector is attached to the outside of the glove.

18. The surgical glove of claim 14, wherein the glove is sterile and impermeable to body fluids.

19. The surgical glove of claim 14, wherein the glove is elastic and conforms tightly to a person's hand.

20. The surgical glove of claim 14, wherein the optical marker is an active optical marker, and wherein the glove further comprises a switch for activating/deactivating the active optical marker.

* * * * *